United States Patent [19]

Cooper et al.

[11] 4,110,439

[45] Aug. 29, 1978

[54] AMINO GLYCOSIDE ANTIBIOTICS HAVING ANTIPROTOZOAL ACTIVITY

[75] Inventors: David J. Cooper, Downingtown, Pa.; Jay Allan Waitz, Fairfield, N.J.; Mae Counelis, New York, N.Y.; Jay Weinstein, Bloomfield, N.J.

[73] Assignee: Schering Corporation, Kenilworth, N.J.

[21] Appl. No.: 752,375

[22] Filed: Dec. 20, 1976

Related U.S. Application Data

[60] Division of Ser. No. 618,647, Oct. 1, 1975, Pat. No. 4,049,796, which is a division of Ser. No. 389,774, Aug. 20, 1973, Pat. No. 3,915,955, which is a continuation-in-part of Ser. No. 48,017, Jun., 1970, abandoned.

[51] Int. Cl.$^2$ .................. A61K 31/71; A61K 31/70
[52] U.S. Cl. ....................................... 424/181; 424/180
[58] Field of Search ............................... 424/180, 181

[56] References Cited

PUBLICATIONS

Chemical Abstracts 65: 11167(d), 1966.

Primary Examiner—Jerome D. Goldberg
Attorney, Agent, or Firm—Stephen B. Coan; Raymond A. McDonald; Carver C. Joyner

[57] ABSTRACT

In the fermentation production of gentamicin C a plurality of additional antibiotic compounds are obtained. Four of these compounds, gentamicin A, gentamicin B, gentamicin $B_1$ and gentamicin X exhibit significant antiprotozoal and anthelmintic activity while gentamicin B and $B_1$ have significant antibacterial properties with markedly reduced side effects.

6 Claims, 8 Drawing Figures

FIG. 1 — GENTAMICIN A SULFATE

FIG. 2 — GENTAMICIN A

FIG. 3 — GENTAMICIN B SULFATE

GENTAMICIN B
FIG. 4

WAVELENGTH (MICRONS)
GENTAMICIN B SULFATE
FIG. 5

GENTAMICIN B
FIG. 6

FIG. 7

FIG. 8

AMINO GLYCOSIDE ANTIBIOTICS HAVING ANTIPROTOZOAL ACTIVITY

This application is a divisional of application Ser. No. 618,647, filed Oct 1, 1975, now U.S. Pat. 4,049,796, issued Sept. 20, 1977 which in turn is a divisional of application Ser. No. 389,774, filed Aug. 20, 1973 now U.S. Pat. 3,915,955 which in turn is a continuation-in-part of application Ser. No. 48,017 filed June 22, 1970 (now abandoned).

FIELD OF INVENTION

This invention relates to antibiotics which possess antiprotozoal and anthelmintic activity and to methods for their production and use. More particularly, this invention relates to antibiotics co-produced with gentamycin, said antibiotics either in admixture with each other or separated one from the other possessing antiprotozoal and/or anthelmintic properties.

BACKGROUND OF INVENTION

The preparation, isolation and purification of gentamycin is described in U.S. Pat. No. 3,091,572. Gentamycin, now known as gentamicin, was described in the patent as the principal antibiotic component and is referred to herein as the C-component or gentamicin C. In the patent, reference is made to co-produced antibiotics BA-3 (Fraction A) and BA-3 (Fraction B) which in admixture with each other exhibited a low order of antibacterial activity. These were separated from gentamicin C.

By the utilization of a particular chromatographic system described later herein, we have found that the substances described in U.S. Pat. No. 3,091,572 as co-produced antibiotics BA-3 (Fraction A) and BA-3 (Fraction B) are not single entities unto themselves but together they represent a mixture of at least four components. Resolution of this mixture of the co-produced antibiotics into its components (hereinafter called gentamicin A, gentamicin B, gentamicin $B_1$ and gentamicin X), has led to the discovery that each member of this group possesses surprising and unexpected applied-use characteristics.

Gentamicin A has been previously isolated in pure form, investigated chemically and biologically and found to have rather weak antibiotic activity. We have discovered the rather surprising applied-use characteristic of gentamicin A, namely, its utility as an antiprotozoal agent. Gentamicin B, gentamicin $B_1$ and gentamicin X heretofore have never been isolated one from the other. We have discovered that these substances possess certain valuable properties as antibiotics, anthelmintic and antiprotozoal agents.

BRIEF DESCRIPTION OF THE INVENTION

We have found that the entire mixture of antibiotics produced by the fermentaion of *Micromonospora purpurea* and *Micromonospora echinospora* as described in U.S. Pat. No. 3,091,572 may be separated by means of a column chromatographic separation process which utilizes the lower layer of a solvent system consisting of methanol, chloroform, and ammonium hydroxide as the eluting solvent. Prior to chromatography, equal volumes of the solvents are mixed, allowed to settle and the layers separated. Gentamicin C, also known as Garamycin ® (Trademark Schering Corporation, Bloomfield, New Jersey) (known to be composed of three components, $C_1$, $C_{1a}$ and $C_2$) is first eluted and is followed in turn by gentamicin $B_1$, gentamicin X, gentamicin B and lastly, gentamicin A. These antibiotics co-produced with gentamicin C and eluted after gentamicin C are structurally similar to each other as shown in formula I which depicts gross molecular arrangement without regard to spatial considerations.

Gentamicin B   $R_1$=CH$_3$ $R_2$=OH  $R_3$=H   $R_4$=NH$_2$
Gentamicin $B_1$ $R_1$=CH$_3$ $R_2$=OH  $R_3$=CH$_3$ $R_4$=NH$_2$
Gentamicin X   $R_1$=CH$_3$ $R_2$=NH$_2$ $R_3$=H   $R_4$=OH wherein $R_1$, $R_2$, $R_3$ and $R_4$ are as defined above.

Gentamicin A and gentamicin X, and to a lesser extent, gentamicin B and gentamicin $B_1$, are effective against such protozoa as *Entamoeba histolytica, Histomonas meleagridis, Trichomonas foetus* and *Trichomonas vaginalis*. *Histomonas meleagridis* is the protozoal parasite which causes enterohepatitis, the so-called "blackhead disease" in turkeys. This disease causes serious economic problems in the turkey raising industry. *Trichomonas vaginalis* is the pathogen most frequently associated with cases of human vaginal infections and is usually a most difficult pathogen to eradicate.

Gentamicin A, gentamicin B, gentamicin $B_1$ and gentamicin X are also effective as anthelmintic agents against pinworms such as *Syphacia obvelata*.

That these substances, gentamicin A, gentamicin B, gentamicin $B_1$ and gentamicin X, possess valuable antiprotozoal properties is surprising. It has been reported that gentamicin C, which is structurally related to the aforementioned antibiotics, exhibits only slight activity against *T. vaginalis* at somewhat high dose ranges. It has been further reported by Albach et al. in the American Journal of Tropical Medicine and Hygiene, 15, 885 (1965) that gentamicin C is relatively ineffective against *E. histolytica*. All of these gentamicin antibiotics are members of a chemical class of compounds sometimes referred to as aminoglycosides. This class includes such known antibiotics as neomycin, kanamycin, streptomycin and paromomycin. Only paromomycin is known to exhibit antiprotozoal activity to any substantial degree. Furthermore, with the exception of paromomycin, gentamicin A, gentamicin B, gentamicin $B_1$ and gentamicin X are the only aminoglycosides now known to exhibit anthelmintic activity in reasonably useful dosage ranges.

In view of these properties gentamicin A, gentamicin B, gentamicin $B_1$ and gentamicin X may be used in vitro in wash solution for sanitary purposes, such as in the cleaning of laboratory equipment contaminated with protozoa of the type named above. This is especially true of laboratory table tops and animal cages and pens from which it is desired to eradicate susceptible parasitic protozoal and bacterial species. By virtue of their in vivo activity, the compounds of this invention may be used in admixture with drinking water or animal feeds to treat laboratory or domestic animals having intestinal bacterial infections, intestinal protozoal infections, and helmintic infestations, or combinations of the foregoing wherein the infecting organisms are susceptible to the compounds of this invention. The compounds are especially useful for intestinal disorders in view of the fact that they are not appreciably absorbed from the gastrointestinal tract. Thus, substantial concentrations of therapeutic agent may be ingested without causing toxic manifestations to the host, and at the same time be present in quantities sufficient to destroy, or at least to substantially inhibit, the infecting organism. For combatting generalized (systemic) bacterial infections administration of antibiotic is efffected by other than oral means, preferably by injection.

SUMMARY OF THE INVENTION

The invention sought to be patented in one of its process aspects resides in the concept of resolving a mixture consisting of gentamicin A, gentamicin B, gentamicin $B_1$ and gentamicin X into the individual antibiotic entities of which the mixture is composed.

The invention sought to be patented in another of its process aspects resides in the concept of combatting bacterial infections in animals which comprises administering to an animal having such an infection a therapeutically effective quantity of a member selected from the group consisting of gentamicin B, gentamicin $B_1$, gentamicin X or their non-toxic pharmaceutically acceptable acid addition salts.

The invention sought to be patented in a further process aspect resides in the concept of treating bacterial infections in animals which comprises administering to an animal having such an infection a therapeutically effective quantity of a mixture containing as the principal active ingredients one or more of the substances of gentamicin B, gentamicin $B_1$, gentamicin X or their non-toxic pharmaceutically acceptable acid addition salts.

The invention sought to be patented in yet another of its process aspects resides in the concept of combatting protozoal infections and/or helmintic infestations which comprises administering to an animal having such an infection or infestation, a therapeutically effective quantity of a member selected from the group consisting of gentamicin A, gentamicin B, gentamicin $B_1$, gentamicin X or their non-toxic pharmaceutically acceptable acid addition salts.

The invention sought to be patented in still another of its process aspects resides in the concept of treating protozoal infections and/or helmintic infestations which comprises administering to an animal, having such an infection or infestation, a therapeutically effective quantity of a mixture containing as the principal active ingredient one or more of the substances gentamicin A, gentamicin B, gentamicin $B_1$ and gentamicin X or the non-toxic pharmaceutically acceptable acid addition salts thereof.

The invention sought to be patented in one of its composition aspects resides in the concept of the novel chemical compounds gentamicin B, gentamicin $B_1$, gentamicin X having the molecular structure as hereinabove described and the non-toxic pharmaceutically acceptable salts of said compounds.

The invention sought to be patented in another of its composition aspects resides in the concept of pharmaceutical compositions for eliciting an antibacterial, an anti-protozoal and/or anthelmintic response which comprises a therapeutically effective quantity a member selected from the group consisting of gentamicin A, gentamicin B, gentamicin $B_1$, gentamicin X a non-toxic pharmaceutically acceptable acid addition salt thereof, or mixtures thereof, and an inert pharmaceutical carrier.

DETAILED DESCRIPTION OF THE INVENTION

Gentamicin A, gentamicin B, gentamicin $B_1$ and gentamicin X have amine or substituted amine groups which are capable of forming non-toxic acid addition salts with organic and inorganic acids. Non-toxic salts are defined herein as those that do not give rise to detrimental side effects when administered at the usual dosage level. Generally, the inorganic acid salts may be formed by adding an amount of dilute (1.0N) acid to an aqueous solution of antibiotic base to adjust the pH of the solution to about 4.5 and lyophilizing the resulting solution. Thus, by the foregoing procedure acid addition salts are formed with hydrochloric acid, sulfuric acid, phosphoric acid and the like including the alkali metal salts of the dibasic and tribasic acids. In general, the salts of inorganic acids are water soluble but are substantially insoluble in organic solvents. However, some such salts (e.g. hydrochlorides) may have very limited solubility in polar organic solvents such as lower alcohols. Salts of organic acids, such as, hydrocarbon carboxylic acids including dibasic acids, such as succinic, tartaric, maleic, fumaric, glutaric and the like are usually prepared by reacting an aqueous solution of the antibiotic with a stoichiometric quantity of acid and either lyophilizing the resulting solution or precipitating the product with a miscible organic solvent such as acetone, dioxane, tetrahydrofuran, methanol or the like.

Gentamicin A, gentamicin B, gentamicin $B_1$ and gentamicin X are obtained from the fermentation as a complex mixture which also includes the major fermentation product, gentamicin C. The gentamicin "C" components constitute from about 60% to about 80% of the mixture and the co-produced antibiotics constitute the remainder. Thus, in order to obtain the co-produced antibiotics it is advantageous to at least partially remove the gentamicin C. There are a substantial number of resins that are suitable for this purpose. Exemplary of such resins are Amberlite IRA-400, Amberlite IRA-401, Dowex 1-X2, and Dowex 2-X4 (Amberlite being a trademark of Rohm and Haas Company, Philadelphia, Pennsylvania) and Dowex being a trademark of Dow Chemical Company, Midland, Michigan). In general, porous, strongly basic quaternary amine type resins are of utility. Applicants prefer to utilize Dowex 1-X2 in the hydroxyl cycle.

At the end of the fermentation, the antibiotics produced therein are extracted from the broth which is accomplished by adsorbing the total antibiotic complex from the fermentation broth onto a cation exchange resin, preferably of the Amberlite type such as IRC-50. The resin is advantageously utilized in the ammonium cycle and the crude antibiotic mixture eluted with dilute ammonium hydroxide. The eluate is decolorized by passage through a column containing a decolorizing carbon, or, preferably, by passage through an anion exchange resin column, especially, a resin of the Amberlite IRA type mentioned above. For decolorizing the IRC-50 resin eluate IRA-401S resin in the hydroxyl cycle is preferred. After decolorization, the eluate is concentrated in vacuo to a solution containing from about 30% to about 60% solids and held for further processing.

At this juncture, the solution contains all of the antibiotics produced in the fermentation and in substantially the ratio produced therein. Removal of the gentamicin C components is effected by adsorbing the concentrate prepared above on a column of a suitable anion exchange resin, such as Dowex 1-X2 and selectively desorbing the gentamicin C components therefrom.

Elution of the gentamicin C components is effected by the use of deionized water having from about 50,000 to about 150,000 ohms resistance. The column may advantageously be connected in series and through a conductivity bridge to an automatic fraction collector so that a sharp rise in conductance of the effluent will actuate the fraction collector. Similarly, a drop in conductance (rise in resistance) followed by a sharp rise in conductance will start the collection of a new fraction. The care with which this column is run, to a substantial degree, controls the quantity of gentamicin "C", which remains in the mixture of co-produced antibiotics and to some degree affects the efficiency of the subsequent (silica gel) column which is used to separate the co-produced antibiotics one from the other.

The co-produced antibiotics are eluted from the Dowex 1-X2 column subsequent to the gentamicin C components and the aqueous eluate concentrated in vacuo to a suitable volume and lyophilized. At this stage, it is advantageous to dissolve the antibiotic mixture in hot methanol and cool while exposing the solution to air. Gentamicin A adsorbs carbon dioxide from the air forming a sparingly soluble carbonate salt which crystallizes from the methanol solution and is removed by filtration and dried in vacuo. The filtrate is concentrated to a residue and dissolved in about 3 volumes of the lower phase of a solvent mixture consisting of methanol:chloroform:ammonium hydroxide in the volume ratio of 1:1:1.

The foregoing solution is placed atop a suitably sized column of silica gel and the column eluted using the abovedescribed solvent mixture and a controlled flow rate. Gentamicin B and gentamicin $B_1$ may be obtained in crystalline form by dissolving the residues from the appropriate column fractions in ethanol and concentrating in vacuo to a residue, redissolving the residue in ethanol and re-evaporating the solution until a crystalline suspension is obtained. This procedure yields substantially pure gentamicin B and gentamicin $B_1$, as ethanol solvates having about 1 mole of ethanol per mole of antibiotic. Gentamicin X is usually obtained as an amorphous solid and, in this connection, behaves like the gentamicin "C" components.

Alternatively, the total antibiotic mixture from the IRA-401S column which includes the gentamicin C components may be subjected to silica gel chromatography. However, the separation effected by this technique is not as sharp as that obtained when most of the gentamicin "C" and the gentamicin A are removed prior to silica gel chromatography.

Gentamicin A, gentamicin B, gentamicin $B_1$, and gentamicin X, after the removal of the gentamicin C components, may be lyophilized and used as a mixture to elicit an antibacterial, antiprotozoal and/or an anthelmintic effect.

The compounds of this invention readily form hydrates and solvates which are extremely difficult to break. Consequently, the physical constants for gentamicin A, gentamicin B and gentamicin $B_1$ are based upon relatively stable hydrates or solvates. Further, although gentamicin B and gentamicin $B_1$ form crystalline ethanol solvates they do not give reproducible melting points but rather tend to soften and eventually become viscous liquids over quite a wide temperature range. Gentamicin X has not yet obtained in crystalline form; it is isolated as a white amorphous solid which likewise has no discrete melting point.

The antibiotics described herein have physical properties substantially as set forth in Table I below:

TABLE I

| Compound | Elemental Calculated | Physical Constants Analyses Found | $[\alpha]_D^{26}$ | Sulfate Salt Analyses | $[\alpha]_D^{26}$ |
|---|---|---|---|---|---|
| Gentamicin A | C = 43.63 | C = 43.60 | +136° | | +96° |
| [1]Calculated for | H = 7.93 | H = 7.86 | (C = 1.0, $H_2O$) | | (C = 0.3, $H_2O$) |
| $C_{18}H_{36}N_4O_{10} \cdot 1.5H_2O$ | N = 11.31 | N = 11.56 | | | |
| | $O^1$ = 37.13 | $O^1$ = 37.16 | | | |
| Gentamicin B | C = 47.70 | C = 47.78 | +155° | C = 30.35 | +116° |
| [1]Calculated for | H = 8.41 | H = 8.38 | (C = 0.3, $H_2O$) | H = 6.59 | (C = 0.3, $H_2O$) |
| $C_{19}H_{38}N_4O_{10} \cdot o_2H_5OH$ | N = 10.60 | N = 10.59 | | N = 7.49 | |
| | $O^1$ = 33.29 | $O^1$ = 33.25 | | S = 8.48 | |
| Gentamicin $B_1$ | C = 47.22 | C = 48.68 | +161° | C = 31.26 | +117° |
| [1]Calculated for | H = 8.34 | H = 8.56 | (C = 0.3, $H_2O$) | H = 6.83 | (C = 0.3, $H_2O$) |
| $C_{20}H_{40}N_4O_{10} \cdot C_2H_5OH$ | N = 10.41 | N = 10.32 | | N = 7.34 | |

TABLE I-continued

| Compound | Elemental Calculated $O^1 = 34.03$ | Physical Constants Analyses Found $O^1 = 32.44$ | $[\alpha]_D^{26}$ | Sulfate Salt Analyses S = 8.72 | $[\alpha]_D^{26}$ |
|---|---|---|---|---|---|
| Gentamicin X | | C = 43.54 | +154° | C = 31.96 | +121° |
| [1]$C_{19}H_{38}N_4O_{10}$ | | H = 7.22 | (C = 0.3,$H_2O$) | H = 6.57 | (C = 0.3,$H_2O$) |
| | | N = 9.90 | | N = 8.64 | |
| | | $O^1$ = 39.34 | | S = 8.70 | |

[1]All oxygen values are by difference

Figure 1:
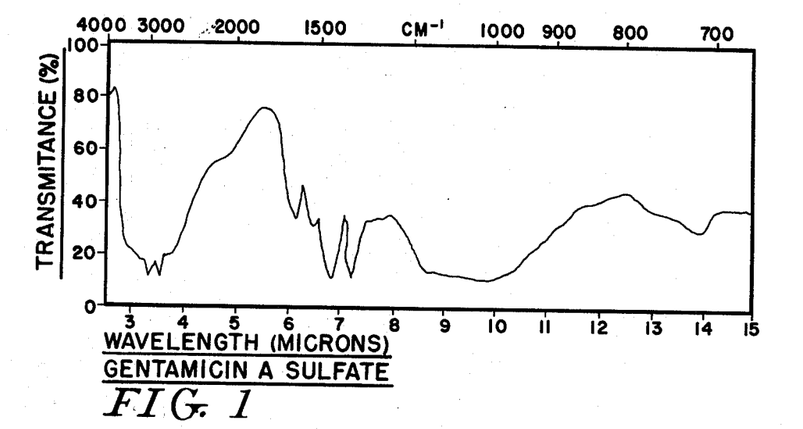
Figure 3:
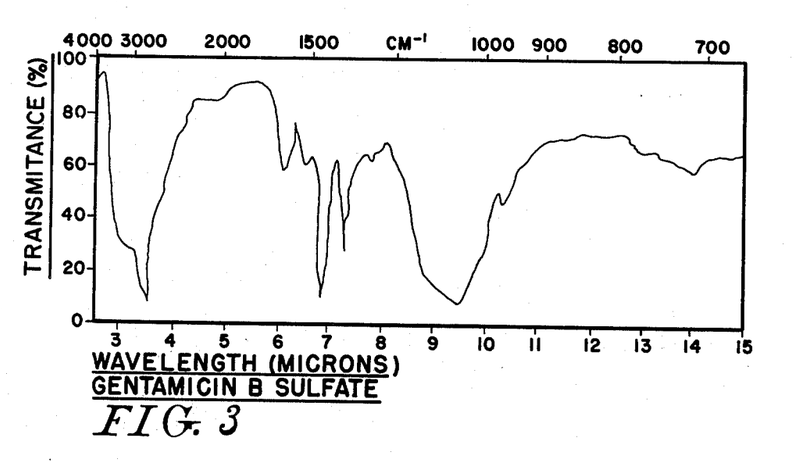
Figure 5:
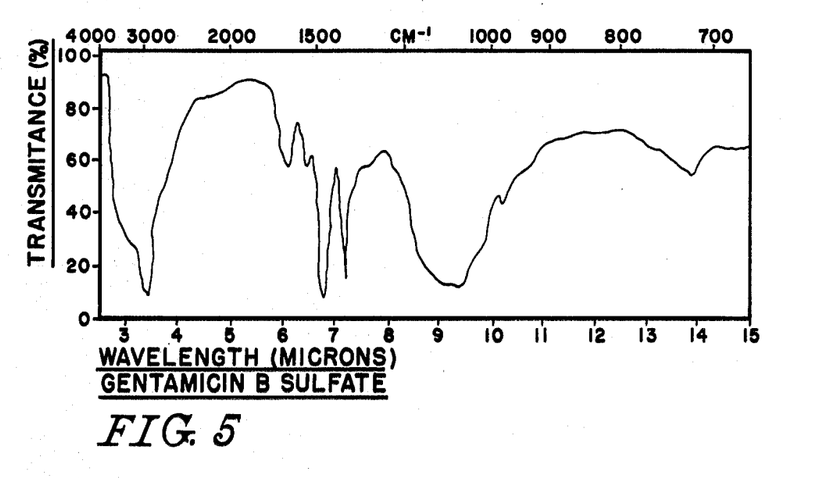
Figure 7:
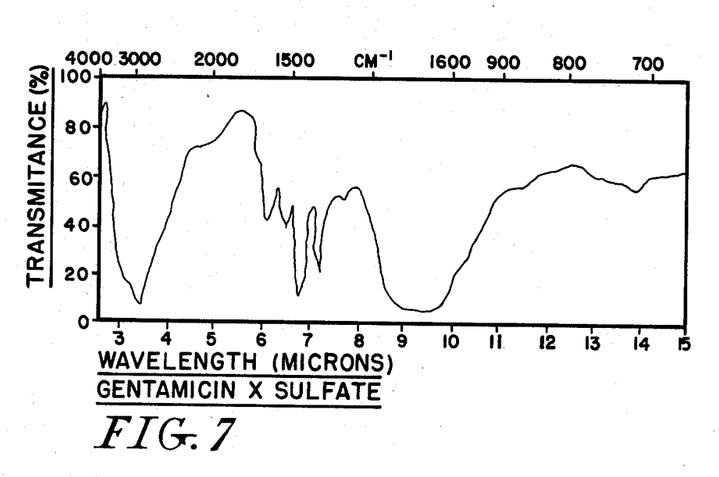

Gentamicin A, gentamicin B, gentamicin $B_1$ and gentamicin X have characteristic infrared absorption spectra in mineral oil (Nujol) as shown by FIG. 1 (gentamicin A), FIG. 3 (gentamicin B), FIG. 5 (gentamicin $B_1$) and FIG. 7 (gentamicin X). These spectra are of the respective antibiotics as sulfate salts.

Figure 2:
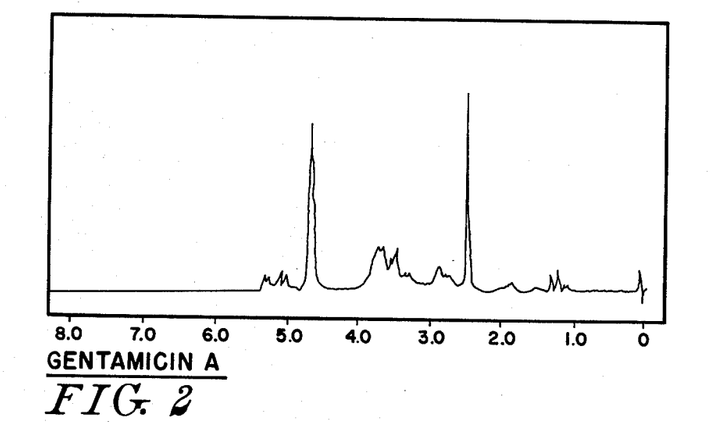
Figure 4:
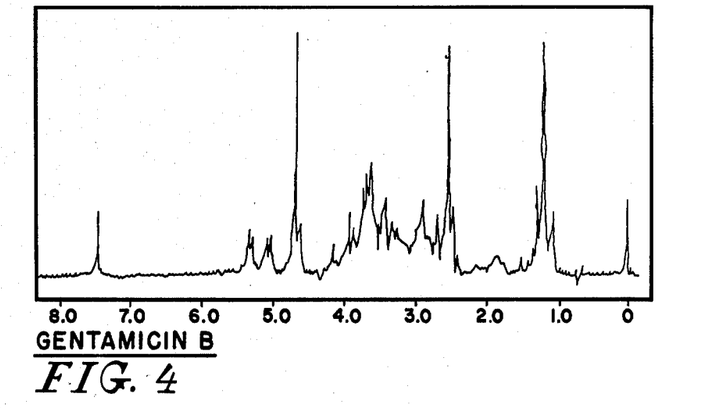
Figure 6:
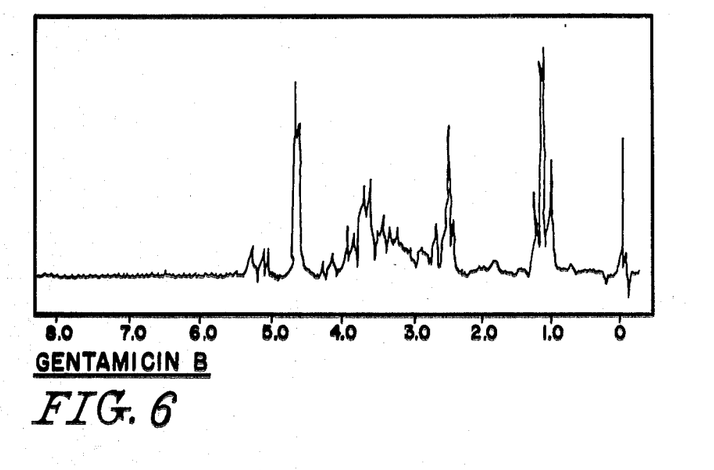
Figure 8:
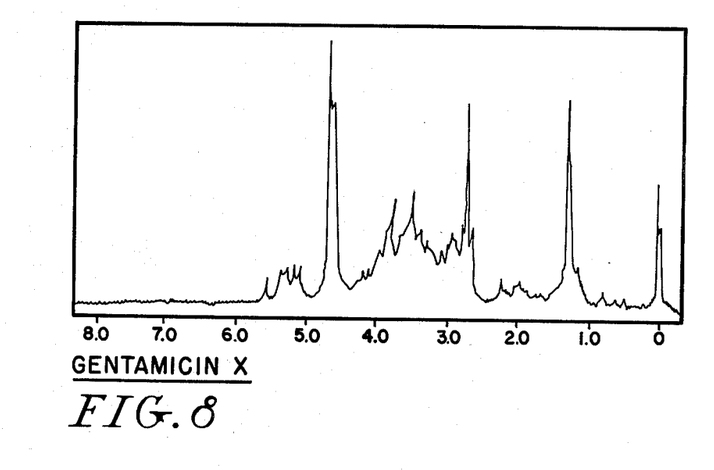

These antibiotics also have characteristic nuclear magnetic resonance spectra (NMR) as shown by FIG. 2 (gentamicin A), FIG. 4 (gentamicin B), FIG. 6 (gentamicin $B_1$), and FIG. 8 (gentamicin X). All of the NMR spectra are of the antibiotic free bases; however, the samples of gentamicin A and gentamicin X were hydrated and those of gentamicin B and gentamicin $B_1$ are of the ethanol solvate. These spectra were obtained by the use of a Varian A-60-A spectrometer (Varian Associates, Palo Alto, California) on about 0.4 ml. of a solution (conc. about 20 mg/ml) of the antibiotic in deuterium oxide ($D_2O$). The spectra are recorded in parts per million (PPM) from 3-(trimethylsilil)-propanesulfonic acid sodium salt, the internal standard.

In Table II below are set forth the more characteristic peaks from FIGS. 1, 3, 5 and 7, respectively.

TABLE II

Significant Infrared Absorption Bands

Gentamicin A Sulfate

| | | | |
|---|---|---|---|
| 2.9 | 3.8 μ (S, V brd) | 6.85 μ | (Nujol) |
| 3.35 | μ (Nujol) | 7.25 μ | (Nujol) |
| 3.55 | μ (Nujol) | 8.50 - 10.75 μ | (V, S, V brd) |
| 4.83 | μ (W, brd) | 12.95 μ | (V, W, brd) |
| 6.17 | μ (M) | 13.88 μ | (W, brd) |
| 6.53 | μ (M) | | |

Gentamicin B Sulfate

| | | | |
|---|---|---|---|
| 2.95 | - 3.25 μ (M-S, brd) | 7.26 μ | (Nujol) |
| 3.40 | μ (Nujol) | 7.75 μ | (W) |
| 3.51 | μ (Nujol) | 8.75 - 9.75 μ | (S, V brd) |
| 4.85 | μ (W, brd) | 10.28 μ | (W-M) |
| 6.16 | μ (M) | 12.95 μ | (VW, brd) |
| 6.55 | μ (M) | 13.90 μ | (W, brd) |
| 6.83 | μ (Nujol) | | |

Gentamicin $B_1$ Sulfate

| | | | |
|---|---|---|---|
| 2.95 | -3.25 μ (M-S, brd) | 7.25 μ | (Nujol) |
| 3.38 | μ (Nujol) | 7.75 μ | (W) |
| 3.50 | μ (Nujol) | 8.75 - 9.75 μ | (S, V brd) |
| 4.85 | μ (W, brd) | 10.27 μ | (W-M) |
| 6.16 | μ (M) | 10.75 μ | (W) |
| 6.55 | μ (M) | 13.05 μ | (V-W, brd) |
| 6.83 | μ (Nujol) | 13.90 μ | (W, brd) |

Gentamicin X Sulfate

| | | | |
|---|---|---|---|
| 3.0 - 3.3 | μ (S, brd) | 7.25 μ | (Nujol) |
| 3.37 - 3.51 | μ (Nujol) | 7.75 μ | (W-M) |
| 3.65 - 4.33 | μ (N, brd) | 8.7 - 10.0 μ | (V-S, brd) |
| 4.82 | μ (W, brd) | 10.30 μ | (Brd, shd) |
| 5.94 | μ (W, shd) | 11.50 μ | (W, brd) |
| 6.17 | μ (M) | 13.03 μ | (V-W, brd) |
| 6.54 | μ (N) | 13.90 μ | (Nujol) |
| 6.83 | μ (Nujol) | 15.08 μ | (V-W) |

Notations: M = medium, S = strong, shd. = shoulder, V = very, W = weak, brd. = broad.

ANTIBIOTIC ACTIVITY - IN VITRO

In Table III below is set forth the in vitro minimal inhibitory concentration of gentamicin B, gentamicin $B_1$ and gentamicin X all in the free base form against a variety of gram positive and gram negative microorganisms. The experiments were carried out in a yeast beef broth medium at pH 7.4.

Table III

| | MIC (mcg/ml)[1] | | |
|---|---|---|---|
| Organism | Gentamicin B | Gentamicin $B_1$ | Gentamicin X |
| Aerobacter aerogenes | 0.08 | 0.08 | — |
| Bacillus subtilis | 0.8 | 3.0 | 0.03 |
| Escherichia coli | 0.03 - 0.3 | 0.08 - 0.3 | 0.3 |
| Klebsiella pneumoniae | 3.0 | 3.0 | 0.75 |
| Pseudomonas aeruginosa | 0.03 - 0.08 | 0.08 | 0.3 - 0.75 |
| Sarcina lutea | 0.3 | 0.3 | — |
| Staphylococcus aureus | 0.3 - 3.0 | 0.3 - 3.0 | 0.08 - 0.75 |
| Streptococcus pyrogenes | 3.0 | 3.0 | 0.3 - 0.75 |
| Shigella sp. M324 | 5.0 | 5.0 | — |
| Salmonella sp. 1 | 0.8 | 0.3 | 0.75 |
| Salmonella sp. 2 | 0.8 | 0.3 | — |
| Salmonella sp. B | 0.8 | 0.3 | — |

ANTIBIOTIC ACTIVITY - IN VIVO

The protective activity of gentamicin B, gentamicin $B_1$ and gentamicin X is determined by administering the respective compound subcutaneously one-hour after administration of an infecting dose of pathogen and by counting the survivors 48 hours after infection. Infected non-treated controls die in about 18 to 24 hours. Generally 5-7 dose levels are administered to mice weighing about 20 grams in groups of 7-10. The $PD_{50}$ values are set forth in Table IV below:

Table IV

| Protective Activity of Gentamicin B, $B_1$ and X in Mice | | | |
|---|---|---|---|
| Injecting Microorganism | Gentamicin B | $PD_{50}$ (mg/kg) Gentamicin $B_1$ | Gentamicin X |
| Staphylococcus aureus Gray | 20.0 | 30.0 | 4.0 |
| Staphylococcus aureus W | 50.0 | 50.0 | — |
| Staphylococcus aureus Smith | 5.0 | 2.5 | — |
| Streptococcus pyogenes C | 15.0 | 18.0 | — |
| Salmonella paratyphi B | 5.0 | 4.0 | — |
| Pseudomonas aeruginosa SC | 2.0 | 2.0 | 7.0 |
| Escherichia coli SC | — | — | 1.5 |

ACUTE TOXICITY

The acute toxicity of gentamicin B, gentamicin $B_1$ and gentamicin X is determined in male CF-1 (Carworth Farms) mice weighing about 20 grams each. The results of this test are set forth in Table V below:

Table V

Acute Toxicity of Gentamicin B, Gentamicin $B_1$ and Gentamicin X

| Route | Gentamicin B | $LD_{50}$ (mg/kg) Gentamicin $B_1$ | Gentamicin X |
|---|---|---|---|
| I.V. | 228 | 230 | 225 |
| I.P. | 1750 | 1600 | >1000 |
| S.C. | >1500 | >1500 | |
| Oral | >250 | >250 | |

IN VITRO ACTIVITY AGAINST TRICHOMONAS VAGINALIS

In Table IV below is set forth the in vitro activity of the compounds of this invention against *T. vaginalis*. The test procedure used was substantially as described by R. J. Schnitzer on pages 289–331 in Experimental Chemotherapy, Volume 1, Academic Press, New York (1963).

Table VI

| Compound | Minimal 99% Suppression Level (mcg/ml) 24 hours | 48 hours | Minimal Cidal level (mcg/ml) 24 hours | 48 hours |
|---|---|---|---|---|
| Gentamicin A | 10 | 5–10 | 25 | 10 |
| Gentamicin B | 25 | 25 | >250 | 25 |
| Gentamicin $B_1$ | 25 | 10–25 | >250 | 25 |
| Gentamicin X | — | 2.5 | — | 10 |
| Garamycin ® | 250 | 100 | >250 | 100 |

STS - Simplified Tripticase Serum Medium, Baltimore Biological Laboratories, Baltimore, Maryland.

Against *Entamoeba hystolytica*, gentamicin X has a minimal inhibitory concentration of 4 mcg/ml (48 hours) and a minimal cidal concentration of 7 mcq/ml (48 hours).

ANTHELMINTIC ACTIVITY IN VIVO

Gentamicin B and gentamicin X exhibit anthelmintic activity against *Syphacia obvelata* when tested in groups of seven male Millerton mice by substantially the procedures described by O. D. Standen on pages 701–892 in Experimental Chemotherapy, Volume 1

Table VII

| Compound | mg/kg/day | %in Diet | % Infected | Mean Worm Burden |
|---|---|---|---|---|
| Gentamicin B | 259 | 0.25 | 0 | 0 |
| Gentamicin B | 100 | 0.0625 | 0 | 0 |
| Gantamicin B | 39 | 0.02 | 0 | 0 |
| Gentamicin B | 8 | 0.008 | 67 | 29.5 |
| Gentamicin X | 310 | 0.25 | 0 | 0 |
| Gentamicin X | 62 | 0.05 | 83 | 27 |
| Controls | 0 | 0 | 100 | 53 |
| Controls | 0 | 0 | 100 | 22 |
| Controls | 0 | 0 | 75 | 6.8 |

The data set forth in Table VII shows that gentamicin B has anthelmintic activity against *Syphacia obvelata* at a minimum dosage of 39 mg/kg/day when administered to male Millerton mice. Gentamicin X is totally effective at 310 mg/kg/day and partially effective at 62 mg/kg/day under substantially the same test conditions.

DIMINISHED INCIDENCE OF ATAXIA

Gentamicin B, and to a lesser extent, gentamicin $B_1$ exhibit a property that is quite unusual in amino-glycoside antibiotics. When subjected to the test procedures described by Weinstein, Wagman and Taber in Antimicrobial Agents and Chemotherapy, 1965, pages 227–231, each of these compounds required substantially longer periods of administration at high doses to cause impairment of the "righting reflex" and the appearance of ataxia. There appears to be a causal relationship between high doses of amino-glycoside type antibiotics given over an extended period of time and vestibular damage wherein one of the early manifestations is ataxia. The test results, in Table VIII, show that gentamicin B and gentamicin $B_1$ as compared with gentamicin C (Garamycin) may be used at dosages that are substantially above the normal therapeutic dose. Moreover, they may be used at such dosages for a time interval substantially beyond that normally required to eliminate infection without causing ataxia; and with minimal, if any, toxic manifestations. Thus, gentamicin B and gentamicin $B_1$ represent a substantial improvement over antibiotics of this class (amino-glycoside) that are currently in use.

Table VIII

Chronic Toxicity in Cats After Daily Subcutaneous Dosing

| Antibiotic | Dose (mg/kg/day) | No. of Cats | Average No. Days to become ataxic |
|---|---|---|---|
| Gentamicin $B_1$ | 240 | 1 | 21.0 |
| | 60 | 4 | 69.0 |
| | 40 | 4 | 108.0 |
| Garamycin ® | 60 | 8 | 13.5 |
| | 40 | 11 | 17.5 |
| | 20 | 5 | 31.4 |
| Gentamicin B | 240 | 1 | 21.0 |
| | 60 | 4 | 81.0 |
| | 40 | 4 | >312* |

*Study terminated 2 of the 4 cats had not become ataxic at the end of 385 days; number given is the trucated median.

PROPHYLACTIC ACTIVITY OF GENTAMICIN A IN TURKEYS AGAINST HISTOMONAS MELEAGRIDIS

Gentamicin A was administered to groups of turkeys at dosage levels of 5, 10, and 15 mg. per turkey per day in aqueous solution. Two days after the initiation of the drug, the turkeys were inoculated orally with 500 *Heterakis gallinae ova* (the intermediate host carrier of *Histomonas*). A single group of turkeys received 0.035% of gentamicin A in their feed for six days. Untreated infected controls were also carried in each experiment. The test is continued for twelve days and the birds are autopsied on the thirteenth day. Infection is usually manifested principally in two areas, the cecum and the liver which are the areas examined during the autopsy.

According to the results obtained in the foregoing test, gentamicin A exhibits prophylactic activity in turkeys against *Histomonas meleagridis* at a minimum dosage level of 10 mg. per bird, whereas the untreated controls became infected.

Isolation of Gentamicin C and the Co-produced Antibiotics from the Fermentation

Adjust the pH of the fermentation broth obtained as described in U.S. Pat. No. 3,091,572 to pH 2.0 with 6N sulfuric acid. Stir the mixture for about 30 minutes and filter through a suitably sized filter which has been pre-coated with about a one (1) inch layer of filter aid. Re-adjust the pH of the filtrate to about 7 with 6N ammonium hydroxide and add oxalic acid to lower the pH to about 4. This quantity of oxalic acid is usually sufficient to precipitate the calcium ions in the fermentation broth as the insoluble calcium oxalate. Adjust the pH to about 7 with 6N ammonium hydroxide and stir the mixture for from about 1 to about 4 hours at about 20°–35° C. Refilter the mixture using a suitably sized pre-coated filter and save the filtrate. Adsorb the antibiotic mixture on IRC-50 (ammonium cycle) using about 10 grams of resin per liter of the original broth volume. Wash the resin color free with deionized water and elute the antibiotics with 2N ammonium hydroxide. Concentrate the eluate in vacuo to a solution containing about 50% solids.

EXAMPLE 2

Separation of Gentamicin C Components from Gentamicin A, Gentamicin B, Gentamicin $B_1$ and Gentamicin X Charge 45 cu. ft. of Dowex 1-X2 resin (hydroxyl cycle) to a clean chromatographic column which is 3 ft. in diameter, at least 8 ft. high and is connected through a conductivity bridge to a fraction collector. Pump deionized water through the resin bed until the effluent has a resistance of at least 65,000 ohms. Charge an aqueous solution of about 120 liters containing about 60 kilograms of solids (from Example 1) to the column and adsorb the antibiotic mixture by permitting the antibiotic solution to pass through the column at the rate of about 2 liters per minute.

Develop the column with deionized water at the rate of about 2 liters per minute and collect fractions in accordance with the conductance of the eluate. Typically, about seven fractions are collected which vary from about 14 to about 750 liters in volume. The first five fractions comprising about 500 liters contains the bulk of the gentamicin C components. The remaining two fractions comprising about 1500 to 1600 liters contains the bulk of gentamicin A, gentamicin B, gentamicin $B_1$ and gentamicin X. The latter two fractions are combined, concentrated in vacuo to a small volume and either lyophilized or spray dried.

In those instances wherein a mixture of the co-produced antibiotics are to be utilized, either the lyophilized or the spray dried product will suffice.

EXAMPLE 3

Isolation of Gentamicin A

Dissolve 19.8 kilograms of fermentation product from which most of the gentamicin C (Example 2) has been removed in 45 liters of hot methanol. Clarify the solution by filtration. Cool the solution at room temperature with exposure to air and seed with gentamicin A. Gentamicin A crystallizes as its colorless carbonate salt which is filtered, washed sparingly with methanol and dried at 80° C in vacuo to obtain 1119 grams of the product of this example. The mother liquor and washes are combined, concentrated to a residue in vacuo and chromatographed as described in Example 4.

EXAMPLE 4

Chromatographic Separation of Gentamicin B Gentamicin $B_1$ and Gentamicin X

Fill two 5 foot × 4 inch chromatographic columns connected in series with silica gel (e.g. Baker Silica Gel for chromatography) which has previously been conditioned by contact with the lower phase of a 1:1:1 mixture of chloroform, methanol and concentrated ammonium hydroxide. Prepare a solution of 750 grams of the residue from Example 3 in a minimum volume (about 2 liters of the lower layer of the above-described solvent mixture). Place the antibiotic solution stop the first column and elute the column at the rate of about 3 to about 4.5 liters per hour, collecting fractions of approximately two (2) liters. Monitor the effluent by thin layer chromatography on silica gel plates using the same solvent system that is being used on the column. Combine the fraction containing like antibiotics and evaporate to a residue. When the amount of gentamicin B eluted tapers off, the column is eluted with a mixture comprising equal volumes of methanol and concentrated ammonium hydroxide to strip the column. The fractions containing gentamicin B and gentamicin $B_1$ are dissolved in ethanol and concentrated to a residue. Repetition of the foregoing step will result in a crystalline suspension of the ethanol solvate of gentamicin B and gentamicin $B_1$. When the foregoing chromatographic separation is effected, the products are obtained in the amounts and order substantially as shown below:

| Fraction | Amount | $[\alpha]_D^{26°}$ |
|---|---|---|
| Gentamicin C ⎫<br>Gentamicin $B_1$ ⎬<br>Gentamicin $B_1$ ⎭ | 198.6 gms<br>42.0 gms | = 157° |
| Gentamicin $B_1$ ⎫<br>Gentamicin X ⎬<br>Gentamicin X ⎭ | 67.8 gms<br>12.3 gms | = 153.8° |
| Gentamicin X ⎫<br>Gentamicin B ⎬<br>Gentamicin B ⎭ | 74.9 gms<br>85.8 gms | = 132° |
| Gentamicin B ⎫<br>Gentamicin A ⎭ | 165.0 gms | |

The fractions containing mixtures of antibiotics may be rechromatographed to afford more of the individual fractions.

EXAMPLE 5

Preparation of Gentamicin A Sulfate

Dissolve 5.0 grams of gentamicin A in 25 ml. of water and adjust the pH of the solution to 4.5 with 1N sulfuric acid. Treat the solution with about 50 milligrams of decolorizing carbon for about 15 minutes and filter. Pour the filtrate into about 300 milliters of methanol with vigorous agitation, continue the agitation for about 10–20 minutes and filter. Wash the precipitate with methanol and dry at about 60° C in vacuo to obtain the product of this Example.

In like manner, the sulfate salt of gentamicin B, gentamicin $B_1$ and gentamicin X may be prepared. In order to prepare sulfate salts of a mixture of gentamicin A, B, $B_1$ and X, the lyophilized or spray dried product of Example 2 is treated as described in this example.

EXAMPLE 6

Preparation of Gentamicin $B_1$ Hydrochloride

Dissolve 5.0 grams of gentamicin $B_1$ in 1000 milliters of water. Prepare a column containing 500 grams of weakly basic ion exchange resin in the chloride cycle, preferably, IR-45 (Trademarked product of Rohm and Haas, Philadelphia, Pennsylvania). Pass the antibiotic solution through the column followed by an additional 500 milliters of water. Concentrate the effluent to about 100 milliters in vacuo and lyophilize to obtain the product of this example.

In like manner, the hydrochloride salt of gentamicin A, gentamicin B, and gentamicin X may be also prepared.

The tangible embodiments of this invention (i.e. gentamicin A, gentamicin B, gentamicin $B_1$ and gentamicin X are suitable for oral, topical or parenteral administration. When administered orally they may be compounded in the form of tablets, capsules, elixirs and the like or may even be admixed with animal feed. It is in these dosage forms that the tangible embodiments of this invention are most effective as anthelminthic and antiprotozoal agents. This is especially true wherein they are being used to treat intestinal amoebiasis or non-specific diarrheas. The compounds of this invention may be incorporated into a dosage unit as the sole active ingredient or they may be compounded into dosage units in combination with other active ingredients, such as anti-anxiety agents, it being known that infections and infestations often cause anxiety reactions in animal species. When the animal species is being treated orally, the tangible embodiments of this invention are administered at from about 10 to about 100 mg. per kilogram of body weight per day, preferably divided into from about 2 to about 4 doses.

For topical administration, the tangible embodiments of this invention may be compounded into creams, ointments, suppositories and the like. Such dosage forms should contain from about 1 to about 10% of antibiotic and should be administered to the site of the infection from about 2 to about 4 times a day.

As shown hereinabove, (see Table VIII) gentamicin B, and gentamicin $B_1$, by virtue of their low ataxic potential, may be used to treat deep-seated bacterial infections especially those which have proved to be refractory to other antibacterial agents. It is preferred that gentamicin B and/or gentamicin $B_1$ be administered parenterally in dosages ranging between about 2 and about 10 mg. per kilogram of body weight per day in divided doses.

The examples below set forth some of the various dosage forms into which the tangible embodiments of this invention may be compounded.

Example 7

| PARENTERAL SOLUTION | mg/ml | mg/10 ml. |
|---|---|---|
| Gentamicin B (as the sulfate) | 40 to 200 mg* | 400–2000 |
| Methylparaben | 1.8 mg. | 18 mg. |
| Propylparaben | 0.2 mg. | 2 mg. |
| Water for Injection q.s. | 1.0 ml. | 10.0 ml. |

*Based on theoretical 100% purity.

Place 70% of the water for injection into a suitable mixing vessel and heat to 70° C. Add the methylparaben and propylparaben and mix until dissolved. Cool the above solution to 25°–30° C. Pass a stream of nitrogen gas through the solution. Add the gentamicin B (as the sulfate) and mix until dissolved. Bring the solution to final volume. Pass the solution through a suitable sterilizing filter, employing appropriate aseptic techniques. Fill the solution into suitable sterile containers employing appropriate aseptic filling techniques.

Example 8

| PARENTERAL SOLUTION | mg/ml | mg/10 ml. |
|---|---|---|
| Gentamicin A (as the Sulfate) | 40 to 200 mg* | 400–2000 |
| Methylparaben | 1.80 | 18.00 |
| Propylparaben | 0.20 | 2.00 |
| Sodium Bisulfite | 3.20 | 32.0 |
| Disodium Edetate, Dihydrate | 0.10 | 1.00 |
| Glacial Acetic Acid | 1.25 | 12.50 |
| Sodium Acetate | 2.50 | 25.00 |
| Propylene Glycol | 100 to 400 | 1000–4000 |
| Water for Injection q.s. | 1.0 ml | 10.00 ml |

*Based on theoretical 100% purity.

Place 70% of the water for injection into a suitable mixing vessel and heat to 70° C. Add the methylparaben and propylparaben and mix until dissolved. Cool the above solution to 25°–30° C. Pass a stream of nitrogen gas through the solution. Add the disodium edetate, dihydrate, sodium acetate and glacial acetic acid; mix thoroughly. Stop the nitrogen sparging, add the sodium bisulfate and mix until dissolved. Add the propylene glycol and mix thoroughly. Add the gentamicin A (as the sulfate) and mix until dissolved. Bring the solution to final volume. Pass the solution through a suitable sterilizing filter, employing appropriate aseptic techniques. Fill the solution into suitable sterile containers employing appropriate aseptic filling techniques.

Example 9

| PARENTERAL SOLUTION | mg/ml | mg/100 ml |
|---|---|---|
| Gentamicin $B_1$ (as the Sulfate) | 40 to 200 mg* | 4000–20,000 |
| Methylparaban | 1.80 | 180 |
| Propylparaben | 0.20 | 20 |
| Sodium Bisulfite | 3.20 | 320 |
| Disodium Edetate, Dihydrate | 0.10 | 10 |
| Glacial Acetic Acid | 1.25 | 125 |
| Sodium Acetate | 2.50 | 250 |
| Water for Injection q.s. | 1.00 ml | 100 ml |

*Based on theoretical 100% purity.

Place 70% of the water for injection into a suitable mixing vessel and heat to 70° C. Add the methylparaben and propylparaben and mix until dissolved. Cool the above solution to 25°–30° C. Pass a stream of nitrogen gas through the solution. Add the disodium edetate, dihydrate, sodium acetate and acetic acid; mix thoroughly. Stop the nitrogen gas, add the sodium bisulfate and mix until dissolved. Add the gentamicin $B_1$ (as the sulfate) and mix until dissolved. Bring the solution to final volume. Pass the solution through a suitable sterilizing filter, employing appropriate aseptic techniques. Fill the solution into suitable sterile containers employing appropriate aseptic filling techniques.

Example 10

| ORAL SYRUP | PER LITER |
|---|---|
| Gentamicin A (as the sulfate) | 100 g.* |
| Standard Granulated Sugar | 550 |
| Sorbitol Solution | 200 |
| Water, to make | 1.0 liter |

*Based on theoretical 100% purity.

Add the gentamicin A (as the sulfate), granulated sugar and sorbitol solution, to approximately 350 mls of water contained in a suitable mixing vessel. Mix until a solution is obtained. Add sufficient water to make 1 liter. Pass the solution through a suitable clarifying filter.

Example 11

| ORAL SYRUP | PER LITER |
|---|---|
| Gentamicin B (as the sulfate) | 100 g.* |
| Granulated sugar | 100 |
| Glucose Syrup | 44 |
| Sorbitol Solution | 400 |
| Glycerin | 50 |
| Alcohol | 50 |
| Water to make | 1.0 liter |

*Based on theoretical 100% purity.

Add the gentamicin B (as the sulfate), granulated sugar, glucose syrup, sorbitol solution, glycerin, alcohol to approximately 500 ml. of water contained in a suitable mixing vessel. Mix until a solution is obtained. Add sufficient water to make 1 liter. Pass the solution through a suitable clarifying filter.

Example 12

| TOPICAL CREAM | PER KG. |
|---|---|
| Gentamicin A (as the sulfate) | 10 g.-100 g. |
| Stearic Acid | 60 g. |
| Propylene Glycol Monostearate | 100 |
| Isorpopyl Myristate | 80 |
| Polyoxyethylene (20) Sorbitan Monopalmitate | 60 |
| Sorbitan Solution | 20 |
| Water to make | 1.0 kg. |

*Based on theoretical 100% purity.

Add the stearic acid, propylene glycol monostearate, isopropyl myristate and polyoxyethylene (20) sorbitan monopalmitate to a suitable mixing vessel. Heat to 80° C. to melt. Mix.

Example 13

| TOPICAL CREAM | PER KG. |
|---|---|
| Gentamicin B (as the sulfate) | 10 g. - 100 g.* |
| Ethoxylated Cetyl/Stearyl Alcohol | 20 g. |
| Cetyl Alcohol | 35 |
| Stearyl Alcohol | 35 |
| Petrolatum | 200 |
| Mineral Oil | 50 |
| Water to make | 1.0 kg. |

*Based on theoretical 100% purity.

Add the cetyl alcohol, stearyl alcohol, ethoxylated cetyl/stearyl alcohol, petrolatum and mineral oil to a suitable mixing vessel. Heat to 80° C. to melt. Mix. Add the gentamicin B (as the sulfate) in approximately 95% of the water heated to 80° C. in a suitable mixing vessel. Mix. Add the melted wax phase to the aqueous phase and mix while cooling to approximately 40° C. Add sufficient water to make 1 kg. Mix until cool.

Example 14

| TOPICAL OINTMENT | PER KG. |
|---|---|
| Gentamicin B$_1$ (as the sulfate) | 10 g. - 100 g.* |
| White Petrolatum, to make | 1.0 g. |

*Based on theoretical 100% purity.

Melt and heat the petrolatum to 50° C. in a suitable mixing vessel. Remove a portion of the melted petroleum and make a slurry of the gentamicin B$_1$ (as the sulfate). Pass the slurry through a suitable colloid mill and mill until a uniform dispersion is obtained. Add the milled slurry to the remainder of the melted petrolatum and mix until cool.

Example 15

| TABLETS | A<br>10 mg Tab. | B<br>25 mg Tab. | C<br>100 mg Tab. |
|---|---|---|---|
| Mixture of Gentamicin A, B, B$_1$ and X (as the Sulfate) | 17.50 mg.* | 43.75 mg.* | 175.00 mg.* |
| Lactose, Impalpable Powder | 197.50 | 171.25 | 126.00 |
| Corn Starch | 25.00 | 25.00 | 35.00 |
| Polyvinylpyrrolidone | 7.50 | 75.0 | 10.50 |
| Magnesium Stearate | 2.50 | 2.50 | 3.50 |
| | 250.00 | 250.00 | 350.00 |

*Based on 60% potency, plus 5% excess.

Prepare a slurry consisting of the mixture of gentamicin A, B, B$_1$ and X (as the sulfate) from Example 2, lactose and polyvinylpyrrolidone. Spray dry the slurry. Add the corn starch and magnesium stearate, and mix. Compress into tablets using suitable tableting equipment.

Example 16

| HARD GELATIN CAPSULES | A<br>10 mg Cap. | B<br>25 mg Cap. | C<br>100 mg Cap. |
|---|---|---|---|
| Gentamicin A, B, B$_1$ and X (as the sulfate) | 17.50 mg* | 43.75 mg.* | 175.00 mg.$^a$ |
| Lactose, Impalpable Powder | 231.50 | 205.25 | 124.25 |
| Magnesium Stearate | 1.00 | 1.00 | 0.75 |

*Based on 60% potency, plus 5% excess.

Place the mixture of gentamicin, A, B, B$_1$ and X (as the sulfate) and lactose into a suitable mixing bowl and mix. Pass the mixed powders through a mill. Add the mixed milled powders to a suitable mixing vessel and mix again. Pre-mix the magnesium stearate with a portion of the batch from above. Pass the premixed magnesium stearate to the batch and mix. Fill into empty gelatin capsules using suitable encapsulating equipment.

Example 17

| BOLUS | 100 mg Bolus |
|---|---|
| Mixture of Gentamicin A, B, B$_1$ and X (as the sulfate) | 175.00 mg.* |
| Lactose | 4335.00 |
| Corn Starch Pregelatinised | 1080.00 |
| Magnesium Stearate | 90.00 |
| Water | 100.0 ml. |
| | 10,000.00 |

*Based on a 60% potency, plus 5% excess.

Place the mixture of gentamicin A, B, B$_1$ and X (as the sulfate), lactose and a portion of the corn starch into a suitable mixing bowl and mix. Prepare a paste of a portion of the corn starch and use this paste to prepare a damp mass of the above powders. Screen the mass to produce granules. Dry the granules. Reduce the dried granules to specific particle size. Add the magnesium stearate, mix and compress the granulation into tablets using suitable tableting equipment.

Example 18

| BOLUS | 5 g. Bolus |
|---|---|
| Mixture of Gentamicin A, B, B$_1$ and X (as the sulfate) | 8250.00 mg.* |
| Lactose, Impalpable Powder | 8560.00 |
| Polyvinylpyrrolidone | 900.00 |
| Magnesium Stearate | 90.00 |
| Corn Starch | 200.00 |
| | 18,000.00 mg. |

*Based on 60% potency, plus 5% excess

Prepare a slurry consisting of the mixture of gentamicin A, B, B₁ and X (as the sulfate), lactose and polyvinylpyrrolidone. Spray dry the slurry. Add the corn starch and magnesium stearate, and mix. Compress into tablets using suitable tableting equipment.

Example 19

| PARENTERAL SOLUTION | mg/ml |
| --- | --- |
| Gentamicin X (as the sulfate) | 40 to 200 mg.* |
| Methylpraben | 1.8 mg. |
| Propylparaben | 0.2 mg. |
| Water for Injection q.s. | 1.0 ml. |

*Based on theoretical 100% purity.

Place 70% of the water for injection into a suitable mixing vessel and heat to 70° C. Add the methylparaben and propylparaben and mix until dissolved. Cool the above solution to 25°–30° C. Pass a stream of nitrogen gas over the solution. Add the gentamicin X (as the sulfate) and mix until dissolved. Bring the solution to final volume. Pass the solution through a suitable sterilizing filter, employing appropriate aseptic techniques. Fill the solution into suitable sterile containers employing appropriate aseptic filling techniques.

Example 20

| ANIMAL FEED | gm |
| --- | --- |
| Mixture of Gentamicin A, B, B₁ and X (as the sulfate) | 10* |
| Soybean meal | 400 |
| Fish meal | 400 |
| Wheat Germ Oil | 50 |
| Sorghum Molasses | 140 |

*Based on 100% purity

Mix all of the above ingredients thoroughly and press into suitably sized pellets, the size of the pellet depending upon animal being treated. Mix the pellets with the animal's regular diet in such a quantity that from about 10 to about 100 mg. per kgs. of body weight is consumed by the animal each day. This composition may be fed to laboratory animals, such as mice, rats, rabbits, cats, dogs and the like.

Alternatively, the antibiotic mixture or a single member thereof may be dry mixed with the animal's regular diet so as to provide a therapeutic dose in a normal day's ration. The method is particularly advantageous when the antibiotics are used to provide a prophylactic effect such as has been previously described for turkeys.

Example 21

| SUPPOSITORY | 5 gm-Suppository |
| --- | --- |
| Mixture of Gentamicin A, B, B₁ and X (as the sulfate) | 5 gm.* |
| Water | 10 ml. |
| Gelatin Granula | 20 gm. |
| Glycerin | 65 gm. |

*Based on theoretical 100% purity

Dissolve the mixture of gentamicin A, B, B₁ and X (as sulfate) in the water and add the glycerin with stirring. Finally, add the gelatin and warm the mixture with stirring until homogeneous. Transfer the mixture to pre-chilled molds and allow to congeal. This formulation is sufficient to prepare twenty 5 gram suppositories.

We claim:

1. A method of treating protozoal infections which comprises administering to an animal having a protozoal infection a therapeutically effective quantity of a member selected from the group consisting of gentamicin A, gentamicin B, gentamicin B₁, gentamicin X, their non-toxic acid addition salts and mixtures thereof.

2. A method of claim 1 wherein the therapeutic effective quantity is from about 10 mg. to about 100 mg. per kilogram of body weight per day.

3. The method according to claim 1 wherein gentamicin A is administered.

4. The method according to claim 1 wherein gentamicin B is administered.

5. The method according to claim 1 wherein gentamicin B₁ is administered.

6. The method according to claim 1 wherein gentamicin X is administered.

* * * * *